United States Patent [19]
Ricci et al.

[11] Patent Number: 4,477,566
[45] Date of Patent: Oct. 16, 1984

[54] METHOD FOR DETERMINATION OF CYTOPLASMATIC AND MITOCHONDRIAL ISOENZYMES OF GLUTAMIC-OXALACETIC TRANSAMINASE IN HUMAN SERUM OR PLASMA

[75] Inventors: Giorgio Ricci; Giorgio Federici, both of Rome, Italy

[73] Assignee: Biodata S.p.A., Italy

[21] Appl. No.: 381,777

[22] Filed: May 25, 1982

[30] Foreign Application Priority Data

May 28, 1981 [IT] Italy ................................ 48565 A/81

[51] Int. Cl.³ .......................... C12Q 1/52; C12Q 1/32; C12N 9/99
[52] U.S. Cl. ....................................... 435/16; 435/26; 435/184
[58] Field of Search ....................... 435/16, 26, 4, 184, 435/193, 810

[56] References Cited

U.S. PATENT DOCUMENTS

| | | | |
|---|---|---|---|
| 3,819,488 | 6/1974 | Rush et al. | 435/16 |
| 4,017,365 | 4/1977 | Nakayama et al. | 435/16 |
| 4,306,019 | 12/1981 | Wada et al. | 435/16 |
| 4,329,425 | 5/1982 | Ricci et al. | 435/810 |

OTHER PUBLICATIONS

John et al., Biochemistry, 8(11): 4477–4482, (1969).
Cavallini et al., Chemical Abstracts, 80:34652f, 94–95, (1974).

Primary Examiner—Esther M. Kepplinger
Attorney, Agent, or Firm—Ostrolenk, Faber, Gerb & Soffen

[57] ABSTRACT

The determination of the single enzymatic activities of the cytoplasmatic and mitochondrial isoenzymes of Glutamic-Oxalacetic Transaminase in samples of serum or plasma is effected by determining the GOT activity before and after incubation with L-serine-O-sulphate.

5 Claims, No Drawings

METHOD FOR DETERMINATION OF CYTOPLASMATIC AND MITOCHONDRIAL ISOENZYMES OF GLUTAMIC-OXALACETIC TRANSAMINASE IN HUMAN SERUM OR PLASMA

The present invention relates to a method for determination of transaminases for use in the field of clinical diagnoses.

The glutamic oxalacetic Transaminases (L-aspartate ketoglutarate Aminto Transferase, EC 2.6.1.1.) named GOT, AST or AAT, exists in two forms distinguished electrophoretically with different sub-cellular location:
(1) A cationic isoenzyme associated with mytochondria (m-GOT);
(2) An anionic isoenzyme present in cytoplasma (s-GOT).

The measure of total activity of GOT in plasma is widely employed for diagnosis of myocardial infarction, and its activity level in physiologic liquids has been employed also for diagnosis of other pathologic forms especially in the liver or skeletal musculature level.

The determination methods actually used in clinical practice permit the measuring on biological samples of the total activity of the enzyme, i.e., the sum of the two isoenzymes.

It is important to distinguish the relative activity of the two isoenzymatic forms of glutamic oxalacetic transaminase in order to obtain a more sophisticated means of investigation relating to the status of tissue necrosis.

It was noted for other enzymes, e.g., lactic dehydrogenase (LDH) and creatine kinase, that the appropriate determination of the activity relative to the different isoenzymatic forms permits a higher discriminating power in diagnostic application.

The methods for dosage actually existing for the two enzymatic forms, cytoplasmatic and mitochondrial, of the glutamic oxalacetic-transaminases are based on electrophoretic, chromatographic or immunologic techniques where the prior separation of one isoenzyme from the other is necessary.

The present invention relates to a new method of dosage which permits the individual determination of the activity of the two isoenzymes in serum or plasma samples without the need to separate the two isoenzymes.

The method is based essentially on the well known reaction of L-serine-O-sulphate with the porcine, cytoplasmatic glutamicoxalacetic transaminase that, after different periods of incubation, is deactivated through the formation of a covalent bond between a derivative of the substrate and a reactive group for the active site of the enzyme (R. A. John, P. Fasella: "The reaction of L-serine-O-sulphate with Aspartate Aminotransferase", Biochemistry, Vol. 8 n.11, Nov. 1969).

During the course of experiments it was found, contrary to expectations, that the conditions of incubation for the deactivation of human cytoplasmatic isoenzyme in the presence of the mitochondrial one, does not determine any loss of activity in the latter.

It is therefore possible, through a determination of GOT activity, present in the plasma or serum, before and after cytoplasmatic isoenzyme deactivation incubation with L-serine-O-sulphate, to assess in the first case the total activity sum of the two isoenzymes, and in the second case (after incubation with serine-O-sulphate) the activity of the only mitochondrial isoenzyme. By means of a simple difference, the value of the activity of the cytoplasmatic isoenzyme is obtained.

The experimental conditions of analysis for determination of the activity of the two, mitochondrial and cytoplasmatic, isoenzymes of GOT, are illustrated as follows.

For determination in the serum or plasma, it is preferable to proceed employing two identical aliquots of the same sample, one of which is employed for determination of total activity (sum of the two isoenzymes) while from the other, incubation with serine-O-sulphate, having previously been performed the value of only the mitochondrial isoenzyme is obtained.

From the same sample of serum or plasma, 0.5 ml is withdrawn and placed in two different test-tubes. In the first test-tube (A), 25 microliters of a 2M solution of serine-O-sulphate in $H_2O$, are added, so as to obtain a final approximate concentration of serine-O-sulphate about 50 mM, without an excessive dilution of the sample. In the second test-tube (B), 25 microliters of $H_2O$ are added to obtain the same dilution which was obtained by adding the serine-O-sulphate to the test-tube (A). Incubation is for 30 minutes at room temperature or for 20 minutes at 30° C. At the end of this period, the reaction is complete, i.e. in test-tube (A) a compound derived from serine-O-sulphate (aminoacrylic acid) has formed a covalent bond with a group present in the active site of the cytoplasmatic isoenzyme completely and irreversibly inactivating it, while this period of incubation does not permit an analogous inhibition of mitochondrial isoenzyme.

Therefore the activity in the two test-tubes is determined by employing the Karmen's method, i.e., following the consumption of the reduced form of Nicotinamide Adenine Dinucleotide (NADH) in the coupled reaction of the glutamic oxalacetic transaminase with the malic dehydrogenase.

From the difference of optical densities at 340 nm per minute are obtained the values of enzymatic units per liter of serum or plasma, as follows:
Test-tube (B) = Total units/liter (cytoplasmatic isoenzyme + mitochondrial isoenzyme)
Test-tube (A) = Units/liter of only the mitochondrial enzyme.

From the difference: Unit/liter (B) − Unit/liter (A), the value of unit/liter of the cytoplasmatic isoenzyme which has been completely inactivated in the test-tube (A) is obtained.

EXAMPLE

In order to demonstrate the validity of the method and illustrate its applicaiton, 5 pools of human serum containing different quantities of the two isoenzymes are prepared. The matrix of the five pools consists of human serum with lowest endogenous activity (<5 U/l). To this serum, different quantities of the two isoenzymes, purified by the method according to E. J. Sampson et al. (Chin. Chem. 24,1805,1978) are added. At the end, the 5 pools are constituted as follows:
pool n.1-120 U/l of only cytoplasmatic isoenzyme
pool n.2-112,5 U/l of which 90 U/l of cytoplasmatic isoenzyme 22.5 U/l of mitochondrial isoenzyme
pool n.3-105 U/l of which 60 U/l of cytoplasmatic isoenzyme 45 U/l of mitochondrial isoenzyme
pool n.4-97,5 U/l of which 30 U/l of cytoplasmatic isoenzyme 67.5 U/l of mitochondrial isoenzyme.
pool n.5-90 U/l of the only mitochondrial isoenzyme.

Proceeding to the determination of the isoenzymatic activities according to the method described, the results reported in the Table are obtained as the average of six different determinations (in the table the cytoplasmatic isoenzyme is indicated as s-GOT and the mitochondrial as m-GOT).

TABLE

|  |  | Theoretical Value U/l | Experimental data U/l |
|---|---|---|---|
| pool N. 1 | Total Activity | 120 | 118.5 |
|  | s-GOT | 120 | 118.5 |
|  | m-GOT | — | — |
| pool N. 2 | Total Activity | 112.5 | 114.7 |
|  | s-GOT | 90 | 91.2 |
|  | m-GOT | 22.5 | 23.4 |
| pool N. 3 | Total Activity | 105 | 103.1 |
|  | s-GOT | 60 | 57.3 |
|  | m-GOT | 45 | 47.1 |
| pool N. 4 | Total Activity | 97.5 | 101.3 |
|  | s-GOT | 30 | 31.3 |
|  | m-GOT | 67.5 | 67.9 |
| pool N. 5 | Total Activity | 90 | 88.4 |
|  | s-GOT | — | — |
|  | m-GOT | 90 | 88.4 |

From comparison of the experimental data thus obtained, in respect to theoretical data regarding the isoenzymatic composition, the validity of the method as well as its precision is obvious.

We claim:

1. Method for determination of single enzymatic activities of the cytoplasmatic and mitochondrial isoenzymes of Glutamic Oxalacitic Transaminase (GOT) in samples of serum or plasma, comprising the steps of determining the GOT activity present in serum or plasma before and after cytoplasmatic isoenzyme deactivating incubation with L-serin-O-sulphate to obtain in the first case an enzymatic activity value corresponding to the total sum of activity of the two isoenzymes, and in the second case a value of enzymatic activity corresponding to the activity of only the mitochondrial enzyme, the activity of cytoplasmatic isoenzyme being obtained from the difference of the two above mentioned values.

2. Method according to claim 1, wherein the determination is effected on two identical aliquots of a same sample of serum or plasma.

3. Method according to claims 1 or 2, wherein the determination of the enzymatic activities is effected following the consumption of the reduced form of Nicotinamide Adenine Dinucleotide (NADH) in the coupled reaction of GOT with malic dehydrogenase.

4. Method according to claim 1, wherein the inactivation of cytoplasmatic isoenzyme with L-serine-O-sulphate is obtained through incubation for 30 minutes at room temperature.

5. Method according to claim 1, wherein the inactivation of cytoplasmatic isoenzyme with L-serine-O-sulphate is obtained by incubation for 20 minutes at 30° C.

* * * * *